US006753010B2

(12) United States Patent
Liu et al.

(10) Patent No.: US 6,753,010 B2
(45) Date of Patent: Jun. 22, 2004

(54) SOFT GELATIN CAPSULE CONTAINING ANGELICA OIL

(75) Inventors: Ke Liu, Yantail (CN); Guisheng Li, Yantail (CN); Chengjun Ma, Yantail (CN); Sheng Yan, Yantail (CN); Xiangyu Li, Yantail (CN)

(73) Assignee: Shandong Luye Phamaceutical Co., Ltd., Yantail (CN)

( * ) Notice: Subject to any disclaimer, the term of this patent is extended or adjusted under 35 U.S.C. 154(b) by 331 days.

(21) Appl. No.: 09/797,651

(22) Filed: Mar. 1, 2001

(65) Prior Publication Data

US 2002/0090393 A1 Jul. 11, 2002

(30) Foreign Application Priority Data

Mar. 1, 2000 (CN) ......................................... 00103336 A

(51) Int. Cl.7 ................................................. A61K 9/48
(52) U.S. Cl. ....................... 424/455; 424/451; 424/456; 514/783
(58) Field of Search ................ 424/451, 452, 424/453, 455, 456

(56) References Cited

U.S. PATENT DOCUMENTS 4,382,924 A * 5/1983 Berling et al. ............... 424/180
6,258,380 B1 * 7/2001 Overholt ..................... 424/456

FOREIGN PATENT DOCUMENTS

CN     87101266      9/1991

* cited by examiner

Primary Examiner—James M. Spear
(74) Attorney, Agent, or Firm—Christie, Parker & Hale, LLP

(57) ABSTRACT

The present invention relates to a soft gelation capsule containing angelica essential oil which consists of capsule material and medicinal oil. Wherein the medicinal oil consists of angelica essential oil and vegetable oil with a weight ratio of 1:0–30. The capsule materials consist of gelatin, glycerol, water and $Fe_2O_3$. Among them angelica essential oil is preferably prepared with the method of $CO_2$-supercritical extraction. The soft gelation capsule containing angelica essential oil retains ligustilide as a principal active constituent in angelica essential oil with a maximal limitation.

18 Claims, No Drawings

SOFT GELATIN CAPSULE CONTAINING ANGELICA OIL

CROSS-REFERENCE TO RELATED APPLICATION

This application claims priority of Chinese patent application number 2000-00103336.0, filed Mar. 1, 2000.

The present invention relates to a novel dosage form of angelica essential oil (soft gelation capsule containing angelica essential oil) and preparation thereof.

The available dosage form of angelica essential oil at present is under the Chinese name of Fu Tong Ning, a kind of dropping pill which has been taken on <<Drug Standard $WS_3$-B-3191-98>> of the Ministry of Public Health, PRC. Among them the standard of angelica essential oil, as an active constituent has been taken on the <<Local Standard of Gansu Province (GWYZZ (85) No. 584>> and the medicinal material, *Angelica sinensis* has been taken on the <<Pharmacopeia of the People's Republic of China>> 1995 Edition, Part 1. The process for preparing said dropping pill is as follows: Angelica essential oil is poured into a mixed liquor of polyethylene glycol 6000 (melted at 100–110° C.) and stearic acid, then it is mixed homogenously and prepared with the method of dropping and enteric coating. The product is thus made. Angelica essential oil used for preparing Fu Tong Ning dropping pill is extracted from the crude drug (Chinese angelica root) by means of steam distillation. The modern pharmaceutical research has proved that angelica essential oil possesses the action of dual-directional regulation on uterine smooth muscle. A further study has discovered that the principal active ingredient in angelica essential oil is ligustilide which possesses a stronger anticholinergic action. However, ligustilide can isomerize easily and the therapeutic effects of the drug are influenced by deactivation due to the partial isomerization of ligustilide under the circumstance of high temperature. Even so, in the case of the original dropping pill the preparation of angelica essential oil is carried out under a circumstance of high temperature (100–110° C.). Certainly, it causes isomerization of ligustilide as an active component and the therapeutic effect of drug is finally influenced.

The present invention is just aimed at the existing drawback of dropping pill of angelica essential oil in the prior art, in order to research and develop a soft gelation capsule of new dosage form for angelica essential oil.

The object of the present invention is just to provide a soft gelation capsule of new dosage form for angelica essential oil.

The soft gelation capsule of angelica essential oil in the present invention consists of capsule material and oil with medicinal liquor, in which the oil with medicinal liquor consists of angelica essential oil and vegetable oil as diluents. The weight ratio of two kinds of oil is in 1:0–30 (preferably 1:2–20; more preferably 1:7–10; most preferably 1:9). Among them angelica essential oil can be obtained by employing steam distillation followed by extraction, and also by $CO_2$-supercritical fluid extraction. In the present invention angelica essential oil is preferably obtained by the mean of $CO_2$-supercritical extraction. When this method is adopted for extracting angelica essential oil, the working condition is as follows: pressure, 15–35 Mpa; temperature, 30–55° C.; time for extraction, 2–20 hours; $CO_2$ flow, 1–10 L/kg of *Angelica sinensis*·hour. Optimized conditions for extraction are as follows: pressure, 20–30 Mpa; temperature, 35–50° C.; time for extraction, 5–8 hours; $CO_2$ flow, 2–6 L/kg of *Angelica sinensis*·hour. The vegetable oil may be one oil selected from the group consisting of sesame oil, peanut oil, corn oil, bean oil, almond oil, peach-kernel oil, cotton seed oil, sunflower seed oil, castor oil and olive oil, preferably sesame oil, peanut oil, corn oil, bean oil and olive oil, while corn oil is the best. The capsule materials consist of gum type of material, plasticizer, water and additive. Among them the gum type of material may be gelatin, or Arabic gum or mixture thereof, wherein the preferred is gelatin. Among them the gelating strength of gelatin is generally in the range of 150–250 brumk and the range of viscosity is 25–45 mPa·S. The plasticizer may be glycerin, sorbitol or mixture thereof. Among them glycerin is preferred. Additive agents may be an antiseptic, such as a mixture of methyl p-hydroxybenzoate (1.6%) and propyl p-hydroxybenzoate (0.04%). When the gelatin is selected as gel material, the weight ratio of dried substance of gelatin and plasticizer is in 1:0.4–0.6 and that of water and dried gelatin is in 1: 0.7–1.4. An additional agent may be light-screening agent which can be $Fe_2O_3$, $TiO_2$, pigment, preferably $Fe_2O_3$. Among them the amount of $Fe_2O_3$ is 0.0075–0.75 mg/kg gelatin.

The soft gelation capsule of the present invention can be made by adopting a conventional preparative process for soft gelation capsule, for example, molding method by hand, rotary molding method or dropping method. Generally, the pressing method, such as rotary molding method is selected preferably. If an autorotatory capsule pressing is employed, the temperature is controlled at 40–50° C., in order to make each capsule containing 10 mg of angelica essential oil.

Soft gelation capsule as the new dosage form of angelica essential oil in the present invention has overcome the drawback in the original dosage form of angelica essential oil as dropping pill because a principal constituent in angelica essential oil is ligustilide which can easily isomerized under an environment of high temperature (such as 100° C.) and thus the content of angelica essential oil is decreased. However, the content of ligustilide in angelica essential oil is relatively stable under the room temperature of 20° C. (see also Example 1 in detail ). The fact that angelica essential oil in dropping pill is added with stirring and dissolving into a mixture of completely melted (100–110° C.) polyethylene glycol 6000 and stearic acid obviously cause an considerable decreasement of content of ligustilide in angelica essential oil. As a result, soft gelation capsule is prepared under temperature of 40–50° C. by press method and the amount of ligustilide in angelica essential oil is this be greatly preserved.

Furthermore, the present invention not only avoid the loss of ligustilide in angelica essential oil by changing dosage form of angelica essential oil, but also obtain angelica essential oil containing higher content of ligustilide by means of improving extraction of angelica essential oil, such as $CO_2$-supercritical extraction under a condition of low temperature. In prior art angelica essential oil is extracted with the traditional process of steam distillation. This method causes some trouble to lower the content of ligustilide in angelica essential oil due to unstability of ligustilide to heat. Making a comparison between steam distillation and $CO_2$-supercritical extraction by means of GC-MS analysis, it has been found that the chemical composition of volatile components of angelica essential oil obtained from the above-mentioned two extraction methods are basically the same, but by means of $CO_2$-supercritical extraction the content of (Z)-ligustilide is increased from 53.99% to 74.54% and (E)-ligustilide 3.18% to 9.11% respectively (see also Example 2).

In short, the present new dosage form (soft gelation capsule containing angelica essential oil) has overcome the drawback from the original one (dropping pill) in many aspects, especially with loss of ligustilide, an active component of angelica essential oil.

Experimental Example 1

Influence of Temperature on Ligustilide Content in Angelica Essential Oil 1.1 Apparatus and Reagents Gas chromatograph (Shimadzu GC-14B); Diethyl phthalate (Shanghai First Reagents Factory, purity is 99.7% tested by gas chromatography with area normalization method); angelica essential oil (991007).

1.2 Experimental Methods

Test group: Five portions of angelica essential oil (30 μl each) are placed separately in five 7 ml-sealing vials numbered with 0, 1, 2, 3 and 4, weighed accurately and sealed. The vials are laid in an oven (100° C.) and the samples are taken out of the oven after 0, 1, 2, 3 and 4 hours respectively. Anabout 16 μl of diethyl phthalate as the internal standard is added. Then the samples are weighed accurately and diluted with ca. 1 ml of ethyl alcohol additionally. According to the method in the item of 【 Purity Test 】 under "Protocol and Remarks of the Quality standard for Angelica essential oil" the content of ligustilide is determined.

Control group: Five portions of angelica essential oil (30 μl each) are placed separately in five 7 ml-sealing vials numbered with 0', 1', 2', 3' and 4', weighed accurately and sealed. The vials are laid aside under room temperature of 20° C. and about 16 μl of diethyl phthalate as internal standard is added after 0, 1, 2, 3 and 4 hours respectively. Accurately and diluted with ca. 1 ml of ethyl alcohol additionally. According to the method in the item of 【 Purity Test 】 under "Protocol and Remarks of the Quality standard for Angelica essential oil", the content of ligustilide is determined.

1.3 Experimental Results

The experimental results show that the content of ligustilide in angelica essential oil decreases gradually when angelica essential oil is under temperature of 100° C., while the content of ligustilide is relatively stable under room temperature (20° C.). The following Table 1 shows the result.

TABLE 1

Content variation of ligustilide under both higher temperature (100° C.) and room temperation (20° C.)

| Condition | Time for determination (Hour) | Content of ligustilide (%) |
|---|---|---|
| higher temperature (100° C.) | 0 | 55.50 |
| | 1 | 41.89 |
| | 2 | 32.74 |
| | 3 | 21.89 |
| | 4 | 12.00 |
| Room temperature (20° C.) | 0 | 55.5 |
| | 1 | 56.01 |
| | 2 | 56.66 |
| | 3 | 55.78 |
| | 4 | 55.39 |

Experimental Example 2: GC-MS Analysis of Angelica Essential Oil Obtained from Different Extraction Material:

Crude drug of Chinese angelica is available in December 1998 from Crude Drugs Supply Center, Min County, Gansu Province, China. The quality examination conforms to the drug standard provided by <<Pharmacopeia of the People's Republic of China>>.

Method:

The conditions for GC-MS are as follows: 25 m×0.2 mm, 5% phenyl polysiloxane (HP-5) chromatographic column; The temperature of column is 80° C. and then raised to 250° C. with a rate of 3° C./min and kept for 10 min. Helium gas is passed with a rate of 0.96 ml/min and the temperature of vaporization chamber is 230° C.

The conditions for mass spectroscopy are as follows: the temperature of ion source and transfer line show 200° C. and 260° C. respectively. Ionization form EI, ionization voltage 70 eV, ionization current 0.22 A, ion source pressure $2.67 \times 10^{-5}$ Pa and mass scanning range 40–350 amu.

The conditions for $CO_2$-supercritical extraction are as follows: pressure 25 Mpa, temperature 40° C., time for extraction 6 hours and $CO_2$ flow, 2 L/kg Angelica sinensis/hour.

Steam distillation is applied for extracting according to the method described in Chinese pharmacopoeia until no distilled oil is found. Table 2 shows the chemical constituent and percentage content of angelica essential oil.

TABLE 2

Chemical constituent and the corresponding percentage content in angelica essential oil obtained from different methods of extraction

| Name or molecular formula | Supercritical extraction | | Steam distillation | |
|---|---|---|---|---|
| | Retention time (min) | Content (%) | Retention time (min) | Content (%) |
| α-Pinene | 3.19 | 1.18 | 3.21 | 3.83 |
| 3,7-Dimethyl-octatriene-[1,3,6] | 4.74 | 4.12 | 4.739 | 20.73 |
| p-Methyl-phenol | 5.47 | <0.2 | — | * |
| 2-Methoxy-phenol | 5.91 | <0.2 | — | * |
| Undecane | — | * | 6.085 | 0.51 |

TABLE 2-continued

Chemical constituent and the corresponding percentage content in angelica essential oil obtained from different methods of extraction

| Name or molecular formula | Supercritical extraction | | Steam distillation | |
|---|---|---|---|---|
| | Retention time (min) | Content (%) | Retention time (min) | Content (%) |
| 1,3,5,5-Tetramethyl-cyclohexa-diene-[1,3] | — | * | 6.898 | <0.2 |
| 6-Butyl-cycloheptadiene[1,4] | 7.74 | 0.47 | 7.740 | 2.79 |
| 6-Undecanone | — | * | 11.392 | <0.5 |
| Tridecane | — | * | 12.386 | <0.5 |
| Phthalic anhydride | 12.94 | — | 12.93 | — |
| Cyclohexendiene[1,3]-1,2-dicarboxylic anhydride | 14.25 | 0.50 | 14.241 | <0.5 |
| 2,4,5-trimethyl benzaldehyde | — | * | 14.455 | <0.5 |
| $C_{15}H_{24}$ (MW = 204) | 16.62 | 0.29 | 16.637 | 1.90 |
| $C_{15}H_{24}$ (MW = 204) | 17.67 | 0.34 | 17.717 | 1.81 |
| $C_{15}H_{24}$ (MW = 204) | 18.232 | 0.34 | 18.297 | 2.13 |
| $C_{15}H_{24}$ (MW = 204) | 19.745 | 0.64 | 18.991 | <0.5 |
| $C_{15}H_{24}$ (MW = 204) | 20.20 | 0.30 | 19.743 | 3.9 |
| $C_{15}H_{24}$ (MW = 204) | 20.22 | <0.5 | 20.24 | 1.80 |
| $C_{15}H_{24}$ (MW = 204) | 21.005 | <0.5 | 21.06 | 0.85 |
| n-Butyl phenyl peptide | 24.78 | 1.10 | 24.774 | 1.16 |
| n-Butenyl phenyl peptide | 25.34 | 1.40 | 25.35 | 1.46 |
| Monoxy-n-butenyl-phenyl peptide | 26.60 | 1.19 | — | * |
| (Z)-Ligustilide | 27.33 | 74.54 | 27.19 | 53.99 |
| (E)-Ligustilide | 28.58 | 9.11 | 28.45 | 3.18 |
| Dioxy-n-butenyl-phenyl peptide | 29.04 | <0.2 | — | * |
| Dioxy-ligustilide | 33.03 | 1.09 | 32.95 | <0.5 |
| Linoleic acid | 35.32 | 0.49 | — | * |

* Not detectable.

The experimental results indicate that the chemical compositions of volatile oil of angelica from two extraction methods are basically the same, but the content of ligustilide in angelica essential oil obtained by using $CO_2$-supercritical extraction method is significantly greater than that of steam distillation method.

EXAMPLES

Example 1

Preparation of Soft Gelation Capsule Containing Angelica Essential Oil a. Preparation of angelica essential oil:
Total volatile oil is obtained from angelica herbal pieces by steam distillation.

b. Gelatin liquor: Gelatin 100 g, glycerin 30 g and water 130 g. A suitable amount of water is added into gelatin which absorbs water to swell. Then glycerol and remaining water are set into a decocting pot, heated at 70–80° C. and mixed homogenously. The swelling gelatin is added with stirring, melted and kept warm for 1–2 hours. The obtained mixture is stood for a certain time, the foam floats on the surface and it must be skimmed. After filtering through a piece of white clean cloth, 0.0075 mg of $Fe_2O_3$ powder is added and mixed homogenously. The product is kept warm and ready for use. The viscosity of the prepared gelatin liquor is generally 2.8–3.2 degree.

c. Preparation of medicinal oil: 10 g of angelica essential oil and 90 g of clear corn oil, stirring sufficiently and homogenously. The product is ready for use.

d. Pressing of soft gelation capsule: The gelatin liquor and angelica essential oil obtained from above is put into an automatically rotatory capsule roller mill and the temperature is controlled at 40–50° C. Each soft gelation capsule which is pressed contains 100 mg of medicinal oil.

Example 2

Preparation of Soft Gelation Capsule Containing Angelica Essential Oil

The procedure is basically identical with that in the Example 1 except any vegetable oil is not added during the preparative procedure of medicinal oil. Finally every pressed soft gelation capsule contains 10 mg of medicinal oil.

Example 3

Preparation of Soft Gelation Capsule Containing Angelica Essential Oil

The procedure is basically identical with that in the Example 1 except angelica essential oil is prepared by using the following procedure: 120 kg of herbal pieces of *Angelica sinensis* are placed in a 600 L supercritical extraction device for $CO_2$-supercritical extraction. During extraction the operative conditions are as follows: pressure: 25 Mpa, temperature: 40° C., time: 6 hours and $CO_2$-flow: 2 L/kg angelica·hour. The extract is filtered and the filtrate is laid aside. Oil layer is finally obtained.

Example 4

Preparation of Soft Gelation Capsule Containing Angelica Essential Oil

The procedure is basically identical with that in the Example 2 except angelica essential oil is prepared by using the following procedure: 120 kg of herbal pieces of *Angelica sinensis* is placed in a 600 L supercritical extraction installation for $CO_2$-supercritical extraction. During extraction the operative conditions are as follows: pressure: 30 Mpa, temperature: 40° C., time: 7 hours and $CO_2$-flow: 4 L/kg angelica·hour. The extract is filtered and the filtrate is laid aside. Oil layer is finally obtained.

Example 5

Preparation of Soft Gelation Capsule Containing Angelica Essential Oil

The procedure is basically identical with that in the Example 1 except 20 g of angelica essential oil and 80 g of clear bean oil are used. The mixed oils are stirred sufficiently and obtained. Finally each pressed soft gelation capsule contains 50 mg of medicinal oil.

Example 6

Preparation of Soft Gelation Capsule Containing Angelica Essential Oil

The procedure is basically identical with that in the Example 1 except 5 g of angelica essential oil and 95 g of clear peanut oil are used. The mixed oils are stirred sufficiently and obtained. Finally each pressed soft gelation capsule contains 200 mg of medicinal oil.

Example 7

Preparation of Soft Gelation Capsule Containing Angelica Essential Oil

The procedure is basically identical with that in the Example 1 except 4 g of angelica essential oil and 96 g of clear peanut oil are used. The mixed oils are stirred sufficiently and obtained. Finally each pressed soft gelation capsule contains 250 mg of medicinal oil.

Example 8

Preparation of Soft Gelation Capsule Containing Angelica Essential Oil

The procedure is basically identical with that in the Example 3 except 5 g of angelica essential oil and 50 g of clear corn oil are used. The mixed oils are stirred sufficiently and obtained. Finally each pressed soft gelation capsule contains 110 mg of medicinal oil.

Example 9

Preparation of Soft Gelation Capsule Containing Angelica Essential Oil

The procedure is basically identical with that in the Example 3 except 5 g of angelica essential oil and 150 g of clear corn oil are used. The mixed oils are stirred sufficiently and obtained. Finally each pressed soft gelation capsule contains 310 mg of medicinal oil.

Example 10

Preparation of Soft Gelation Capsule Containing Angelica Essential Oil

The procedure is basically identical with that in the Example 3 except 5 g of angelica essential oil and 100 g of clear corn oil are used. The mixed oils are stirred sufficiently and obtained. Finally each pressed soft gelation capsule contains 210 mg of medicinal oil.

Example 11

Preparation of Soft Gelation Capsule Containing Angelica Essential Oil

The procedure is basically identical with that in the Example 3 except 10 g of angelica essential oil and 70 g of clear corn oil are used. The mixed oils are stirred sufficiently and obtained. Finally each pressed soft gelation capsule contains 80 mg of medicinal oil.

What is claimed is:

1. A soft gelatin capsule containing angelica essential oil wherein said soft gelatin capsule consists of capsule material and medicinal oil, wherein the medicinal oil consists of angelica essential oil and vegetable oil, the vegetable oil being present in the medicinal oil in an amount up to 30 parts per weight per 1 part per weight of angelica essential oil.

2. A soft gelatin capsule according to claim 1, wherein the weight ratio of angelica essential oil to vegetable oil is 1:2–20.

3. A soft gelatin capsule according to claim 2, wherein the weight ratio of angelica essential oil to vegetable oil is 1:7–10.

4. A soft gelatin capsule according to claim 3, wherein the weight ratio of angelica essential oil to vegetable oil is 1:9.

5. A soft gelatin capsule according to claim 1, wherein the vegetable oil is selected from the group consisting of sesame oil, peanut oil, corn oil, bean oil, almond oil, peach kernel oil, cotton seed oil, sunflower seed oil, castor oil and olive oil.

6. A soft gelatin capsule according to claim 5, wherein the vegetable oil is selected from the group consisting of sesame oil, peanut oil, corn oil, bean oil and olive oil.

7. A soft gelatin capsule according to claim 1, wherein the angelica essential oil is prepared by steam distillation or $CO_2$-supercritical extraction.

8. A soft gelatin capsule according to claim 7, wherein the angelica essential oil is prepared by $CO_2$-supercritical extraction.

9. A soft gelatin capsule according to claim 8, wherein the conditions for $CO_2$-supercritical extractions include a pressure ranging from 15–35 Mpa, a temperature ranging from 30–55° C., a time for extraction ranging from 2–20 hours and a $CO_2$ flowrate ranging from 1–10 L/kg angelica·hour.

10. A soft gelatin capsule according to claim 9, wherein the conditions of $CO_2$-hypercritical extraction include a pressure ranging from 20–30 MPa, a temperature ranging from 35–50° C., a time for extraction ranging from 5–8 hours and a $CO_2$ flowrate ranging from 2–6 L/kg angelica·hour.

11. A soft gelatin capsule according to claim 1, whereto the capsule material consists of gel or gum, a plastifier, water and an additive.

12. A soft gelatin capsule according to claim 11, wherein the gum material is selected from the group consisting of gelatin, arabic gum and mixtures thereof.

13. A soft gelatin capsule according to claim 11, wherein the plastifier is selected from the group consisting of glycerol, sorbitol and mixtures thereof.

14. A soft gelatin capsule according to claim 12, wherein the weight ratio of gelatin to glycerin is 1:0.4-0.6 and the weight ratio of water to gelatin is 1:0.7–1.4.

15. A soft gelatin capsule according to claim 14, wherein the additive is a light-screening agent.

16. A soft gelatin capsule according, to claim 15, wherein the light-screening agent is selected from the group consisting of $Fe_2O_3$, $TiO_2$ and pigments.

17. A soft gelatin capsule according to claim 16, wherein the light-screening agent is $Fe_2O_3$.

18. A soft gelatin capsule according to claim 17, wherein the amount of $Fe_2O_3$ used is 0.0075–0.075 mg/kg gelatin.

* * * * *